United States Patent [19]

Chantry et al.

[11] 4,007,624
[45] Feb. 15, 1977

[54] ELECTRONEGATIVE GAS DETECTION TECHNIQUE

[75] Inventors: Peter J. Chantry; Cheng-Lin Chen, both of Pittsburgh, Pa.

[73] Assignee: Westinghouse Electric Corporation, Pittsburgh, Pa.

[22] Filed: July 2, 1975

[21] Appl. No.: 592,857

[52] U.S. Cl. .................................. 73/23; 324/33
[51] Int. Cl.² ........................................ G01N 27/62
[58] Field of Search ........................ 73/23; 324/33

[56] References Cited

UNITED STATES PATENTS

| 3,211,996 | 10/1965 | Fox et al. | 324/23 |
| 3,238,367 | 3/1966 | Sternberg et al. | 324/33 |
| 3,318,149 | 5/1967 | Varadi | 324/33 |
| 3,803,481 | 4/1974 | Compton et al. | 73/23 X |

OTHER PUBLICATIONS

Lovelock et al., "Electron Capture Ionization Detector", Academic Press, 1962 pp. 219–229.

Primary Examiner—Richard C. Queisser
Assistant Examiner—Stephen A. Kreitman
Attorney, Agent, or Firm—M. P. Lynch

[57] ABSTRACT

The detection of electronegative gases through the use of a dissociative electron attachment process is enhanced by exciting the molecules of an electronegative gas of interest to an electronic or vibrational level to increase the cross section of the molecule for dissociative attachment of electrons to produce negative ions indicative of the gas molecules of interest.

10 Claims, 5 Drawing Figures

ELECTRONEGATIVE GAS DETECTION TECHNIQUE

BACKGROUND OF THE INVENTION

The quantitative detection of minority species is often performed by measuring the charged species arising from the interaction of electrons with the molecules. The sensitivity of such techniques is directly proportional to the cross-section for the reaction involved. For example, in a mass-spectrometer the species M might be detected through the reaction:

$$e + M \rightarrow M^+ + Ze$$

with a cross-section of approximately $10^{-16}$ cm$^2$ for a 70eV electron. In contrast to this technique, some instruments make use of the electronegativity of the molecule to be detected, through a dissociative electron attachment process illustrated by a reaction such as:

$$e + AB \rightleftharpoons (AB^-)^{-*} \rightarrow A + B^-$$

wherein AB is an electronegative molecule capable of disassociatively attaching electrons to form fragments A and B where both A and B may be atoms or molecules.

Reactions of this type have cross-sections ranging from approximately $10^{-13}$ cm$^2$ to approximately $10^{-23}$ cm$^2$, the general trend being for the cross-section to decrease with increasing energy of the attaching electron. Where attachment of very low energy electrons is possible, as is $SF_6$ for example, the cross section is sufficiently large (approximately $3 \times 10^{-14}$ cm$^2$) for a species to be easily detected in a relatively simple electron drift tube device such as the electronegative gas detector described in U.S. Pat. No. 3,211,966, issued Oct. 12, 1965 and assigned to the assignee of the present invention. The sensitivity of such devices to other gases is generally much lower, however, due to the smaller attachment cross-sections.

SUMMARY OF THE INVENTION

There is disclosed herein with reference to the accompanying drawings a technique for increasing the sensitivity of electronegative gas detectors by optically pumping or thermally exciting the molecules into excited states, vibrational and/or electronic, in which they are capable of attaching very low energy electrons, i.e. less than 5 eV, with reasonably large attachment cross-sections, i.e., between $10^{-13}$ cm$^2$ and $10^{-16}$ cm$^2$.

The optical pumping of gas molecules through the use of a laser or other suitable light energy source provides accurate selection of the gas molecule of interest. Typically the energy wavelength suitable for exciting the molecule to satisfy the inventive technique corresponds to the infrared region.

The following reactions are known to have enhanced cross sections when the molecule is in a higher vibrational state:

$$e + O_2 \rightarrow O^- + O$$
$$e + N_2O \rightarrow O^- + N_2$$
$$e + CO_2 \rightarrow O^- + CO$$
$$e + CCl_2F_2 \rightarrow Cl^- + CClF_2$$
$$e + CHClF_2 \rightarrow Cl^- + CHF_2$$

These reactions have been reported and substantiated in the following published references:

*Physics Review*, 183, 157 (1969) by W. Henderson, W. L. Fite and R. T. Brackman

*Physics Review*, 188, 280 (1969) by D. Spence and G. J. Schulz

*Journal of Chemistry and Physics*, 51, 3369 (1969) by P. J. Chantry

Similar effects have been observed in numerous other molecules as reported in an article entitled Associative Thermal Electron Attachment To Some Aliphatic Chloro, Bromo, Compounds, written by W. E. Wentworth, R. George and H. Keith and published in the Journal of Chemical Physics, 51, 1791 (1969).

BRIEF DESCRIPTION OF THE DRAWINGS

The invention will become more readily apparent from the following exemplary description in connection with the accompanying drawings.

DESCRIPTION OF THE INVENTION

Figure 1:
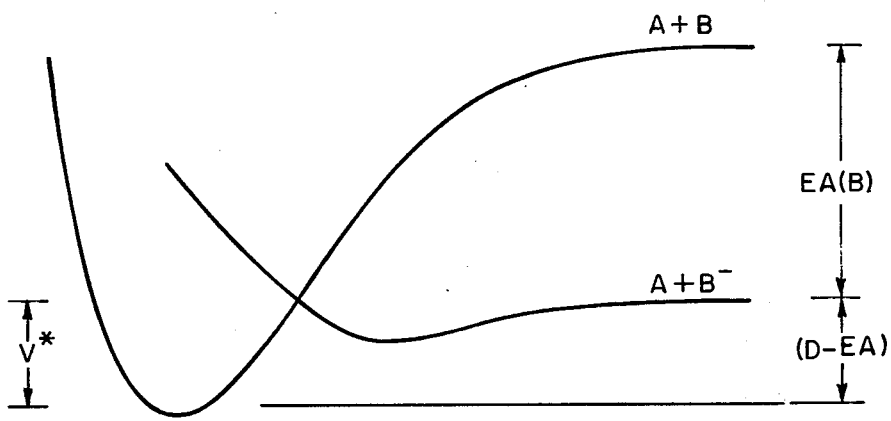
FIGS. 1 and 2 are potential energy diagrams depicting the inventive technique.

The concept of optically pumping molecules such that minority electronegative constituents in air can be detected with enhanced sensitivities by devices serving as leak detectors and pollution monitors is summarized in FIG. 1, which represents a generalized potential energy diagram in which AB is an electronegative molecule capable of disassociatively attaching electrons to form fragments A and B, where both A and B may be atoms or molecules. For example, assuming the electronegative molecule is $CCl_2F_2$, A represents $CClF_2$ and B represents Cl. Referring to FIG. 1, it is noted that the attachment of a zero energy electron requires that the molecule AB be vibrationally excited with energy V* or greater, and that V* ≥ D-EA where D is the energy required to break the A-B bond and EA is the electron affinity of B.

In principle, the attachment cross-section for zero energy electrons interacting with molecules excited vibrationally to levels with energy ≥ V* will be comparable to that in $SF_6$. Thus, if all the molecules of a given species could be given the required degree of vibrational excitation, the sensitivity of the device to that gas could be made comparable to its sensitivity to $SF_6$.

Any means of vibrationally heating the target molecules may be expected to improve the sensitivity of a detector which uses the attachment process as a signature of the gas. This may be done by direct thermal excitation of the gas to temperatures between 300° K and 800° K, or by photo-excitation of the appropriate vibrational modes or by a combination of thermal and photo-excitation. Photo-excitation is, in principle, the most efficient technique since only the vibrational modes of direct benefit in enhancing the attachment cross-section need be excited. Measured activation energies, corresponding approximately to V* in FIG. 1, are usually in the range of 0.1 to 0.5 eV, suggesting that the pumping radiation should be in the range 2 to 12 μ. There are many laser lines in this range. Alternatively a high power lamp having a suitable spectral power distribution could be used.

Figure 2:
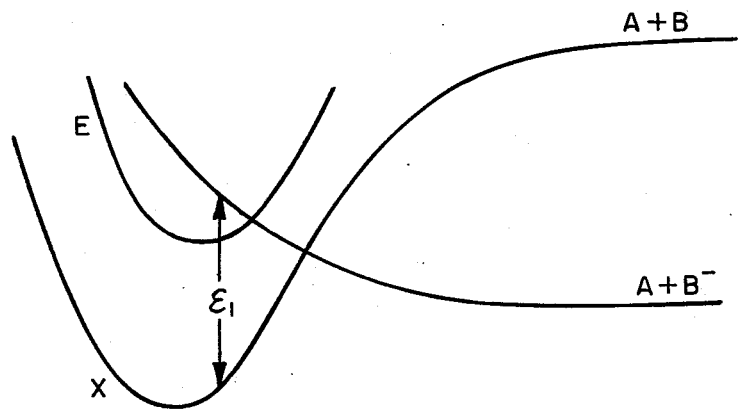

A variation of the mechanism described above is the use of optical excitation of higher electronic states in order to induce dissociative attachment of low energy electrons in gases which would otherwise only attach higher energy electrons, such as CO, $CO_2$, NO, $NO_2$, etc. This situation is represented in FIG. 2, where the curve X represents the ground electronic state of the molecule and E represents an excited electronic state. Attachment of an electron to the ground state (X) to yield the fragments $A + B^-$ occurs only if the electron has energy approximately $\epsilon_1$. If, on the other hand, the molecule is optically pumped to state E, an electron of very low energy can be attached with a much larger cross-section.

Figure 3:
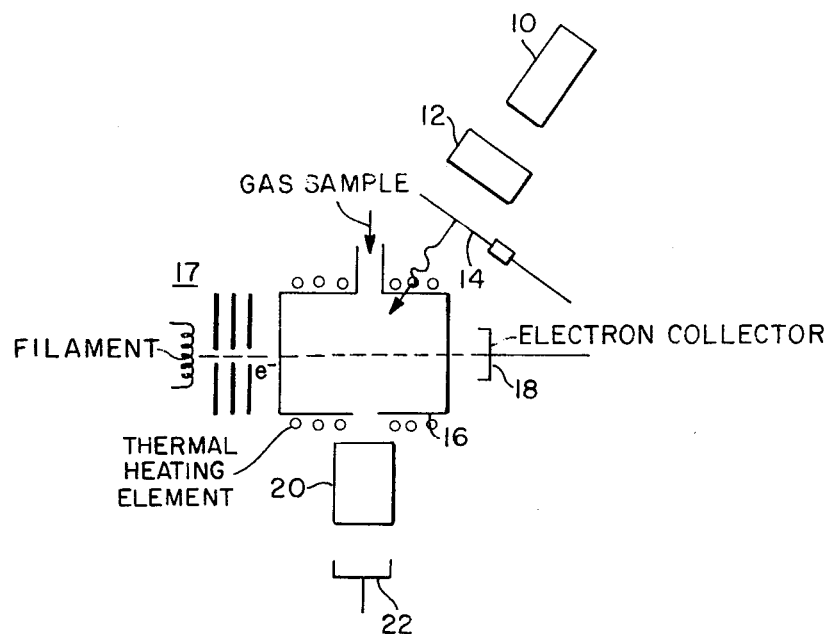
FIGS. 3 and 4 are schematic illustrations of typical embodiments of the inventive technique.
Figure 4:
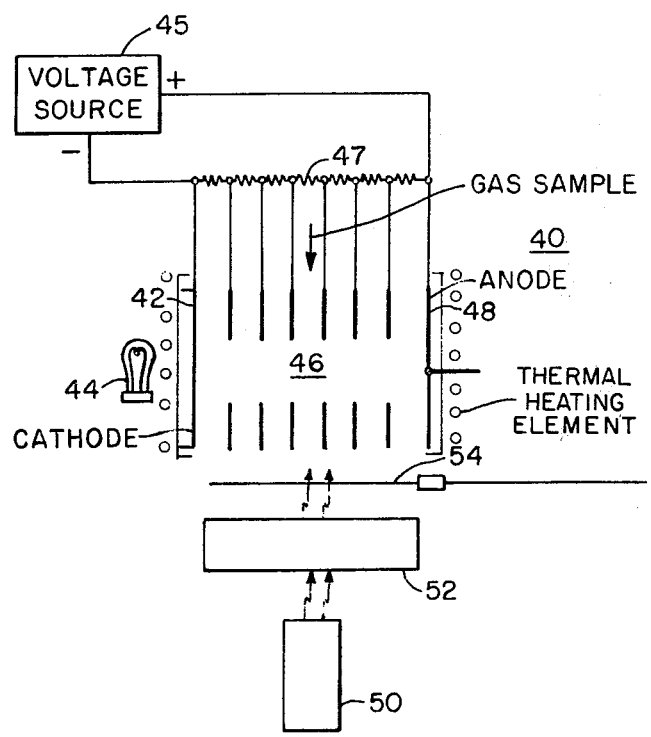
Figure 5:
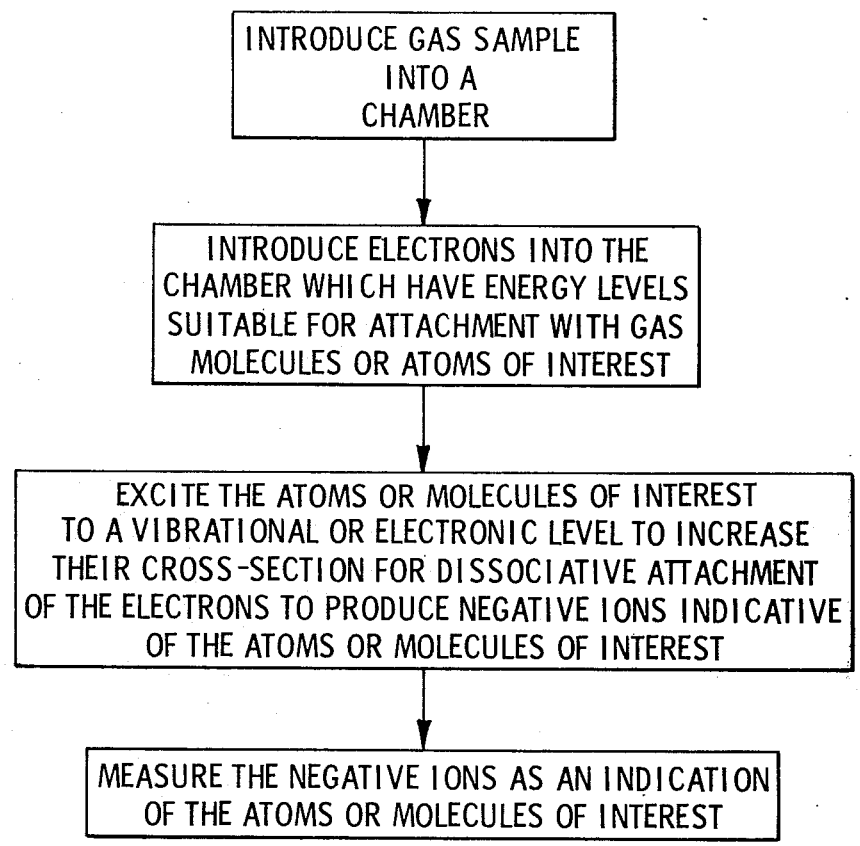
FIG. 5 is a flow chart representation of the method steps defining an embodiment of the invention.

The schematic illustrations of FIGS. 3 and 4 represent typical embodiments based on the above teachings. The embodiment of FIG. 3 represents a modified mass-spectrometer arrangement. A laser or lamp 10 generates a light beam which is transmitted through a lens and filter system 12 and chopper 14 to irradiate the gas sample introduced into chamber 16. The chopper 14 provides effective means for converting the continuous beam into a pulsating beam for irradiating the gas sample. Electrons produced by a cathode 17, shown here as a directly heated filament, are collected by the electron collector 18 with the negative ions produced passing through the massspectrometer 20 is typically tuned to the particular negative ion of interest. Tuning of the system to monitor a particular negative ion can also be accomplished through the use of a laser light source of a wavelength suitable for exciting the molecules of interest or the combination of a light source and filter to irradiate the gas molecules with light energy of the appropriate wavelength.

The embodiment illustrated in FIG. 4 consists of an electron drift cell 40 wherein electrons produced by the photo-cathode 42 in response to impinging light energy from the ultraviolet lamp 44 drift through the gas under the influence of an applied field developed by a voltage source 45 and resistor network 47 and ultimately collected at the anode 48. The loss of electrons through attachment causes a delay in the arrival of the corresponding negative charge at the anode 48. As described in the above-identified reference U.S. Patent, this effect may be measured by pulsing the cathode 42 and using phase sensitive detection of the anode current. In the embodiment illustrated in FIG. 4 the cathode 42 is operated continuously and the pumping light developed by the light source 44 herein represented as UV lamp 50 is transmitted through the lens and filter system 52 and pulsated by the chopper 54. Alternatively both the light from the light source 44 and the pumping light from the laser 50 could be chopped at different frequencies and double phase-sensitive detection used to further improve the signal to noise ratio.

Regardless of the method used to detect the attachment signal, the signal will be proportional to the density N* of attaching molecules in the appropriate excited vibrational states. This is given in general by the following expression:

$$N^* = N_o I_p \sigma_p / (\tfrac{1}{\tau} + N_b \overline{Q} v)$$

where $N_o$ is the density of attaching molecules capable of absorbing the pumping radiation, $I_p$ is the pumping photon flux, $\sigma_p$ is the photo-absorption cross-section, $\tau$ is the radiative lifetime of the excited vibrational state, $N_b$ is the number density of the background gas, $\overline{Q}$ is a collisional quenching cross-section, and $v$ is the relative velocity between the vibrationally excited molecules and the background gas molecules. In the low pressure situation, such as that represented in FIG. 3, it is likely to have $1/\rho \gg N_b \overline{Q} v$. The inequality is likely to be reversed at higher pressures, such as might be used in the embodiment of FIG. 4. In either case N0 $\alpha$ $N_o$ and the attachment signal is proportional to the density of the species being detected.

While the embodiments of FIGS. 3 and 4 employ optical excitation means, it is apparent from the above discussion that a thermal excitation means could be substituted therefore to achieve the desired molecular excitation.

Thermal and/or optical excitation of the vibrational and/or electronic states of gas constituents of interest in accordance with the above teachings will significantly increase the sensitivity of electronegative gas detection techniques. Furthermore, the use of a mass-spectrometer to detect the negative ions produced and the use of pumping radiation tuned to a gas constituent of interest permits desirable gas constituent selectivity capabilities. The sensitivity of the gas detector design in accordance with the above teachings can be varied by varying the intensity of the pumping radiation.

What we claim is:

1. A method for improving the sensitivity of electronegative gas detection techniques employing a dissociative electron attachment process, comprising the steps of,
introducing electrons into a gas, said electrons having a suitable energy for attachment to molecules of interest within said gas,
exciting molecules of interest to a vibrational or electronic level sufficient to increase the cross section of the molecules of interest for dissociative attachment by the electrons to produce negative ions indicative of the molecules of interest, and
measuring the negative ions as an indication of said molecules of interest.

2. A method as claimed in claim 1 wherein the exciting of said molecules is accomplished by optically pumping said gas molecules by a light source.

3. A method as claimed in claim 2 wherein the energy range of said light energy is between 2 and 12 microns.

4. A method as claimed in claim 1 wherein the exciting of said molecules of interest is achieved by direct thermal excitement.

5. A method as claimed in claim 2 further including the step of tuning said optical pumping to an energy suitable for optimum excitation of said molecules of interest.

6. A method as claimed in claim 1 wherein the exciting of said molecules of interest is achieved by a combination of optically pumping the thermal heating of said gas molecules of interest.

7. Apparatus for improving the sensitivity of electronegative gas detection techniques employing a dissociative electron attachment process, comprising,
means for introducing electrons into a gas, said electrons having a suitable energy for attachment to molecules of interest within said gas, and
means for exciting the molecules of interest to a vibrational or electronic level sufficient to increase to cross section of the molecules of interest for dissociative attachment by the electrons to produce negative ions indicative of the molecules of interest, and
means for measuring the negative ions as an indication of said molecules of interest.

8. Apparatus as claimed in claim 7 wherein said means for exciting said molecules includes a light source for emitting light energy in the range 2 microns to 12 microns.

9. Apparatus as claimed in claim 7 wherein said means for exciting said molecules of interest includes direct thermal heating means.

10. Apparatus as claimed in claim 7 wherein said means for exciting said molecules of interest is a combination of a light source optically pumping and a direct thermal heating means.

* * * * *